US 8,285,032 B2

(12) United States Patent
Kawaguchi

(10) Patent No.: US 8,285,032 B2
(45) Date of Patent: Oct. 9, 2012

(54) INSPECTION SYSTEM AND INSPECTION METHOD

(75) Inventor: Hiroshi Kawaguchi, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 12/719,390

(22) Filed: Mar. 8, 2010

(65) Prior Publication Data
US 2010/0158348 A1 Jun. 24, 2010

Related U.S. Application Data

(63) Continuation of application No. 11/251,909, filed on Oct. 18, 2005, now Pat. No. 7,697,746.

(30) Foreign Application Priority Data

Oct. 18, 2004 (JP) ................................. 2004-303172

(51) Int. Cl.
G06K 9/00 (2006.01)

(52) U.S. Cl. ........ 382/149; 382/141; 382/144; 396/104; 359/494

(58) Field of Classification Search .................. 382/149, 382/151, 144, 141; 396/65, 104, 106, 123
See application file for complete search history.

(56) References Cited

U.S. PATENT DOCUMENTS

| 4,595,289 A | * | 6/1986 | Feldman et al. | 356/237.5 |
| 4,698,816 A | * | 10/1987 | Chun | 372/19 |
| 4,720,162 A | * | 1/1988 | Mochizuki et al. | 385/16 |
| 4,866,475 A | * | 9/1989 | Suzuki | 355/38 |
| 5,102,222 A | * | 4/1992 | Berger et al. | 356/367 |
| 5,367,403 A | * | 11/1994 | Yamamoto et al. | 359/489.06 |
| 5,563,649 A | * | 10/1996 | Gould et al. | 348/14.13 |
| 5,890,095 A | * | 3/1999 | Barbour et al. | 702/40 |
| 6,055,066 A | * | 4/2000 | Kanda | 358/461 |
| 6,396,943 B2 | * | 5/2002 | Yamashita | 382/144 |
| 6,512,578 B1 | * | 1/2003 | Komatsu et al. | 356/237.5 |
| 6,656,648 B2 | * | 12/2003 | Inoue | 430/30 |

(Continued)

FOREIGN PATENT DOCUMENTS

JP 10-224529 A 5/1998

(Continued)

OTHER PUBLICATIONS

Japanese Office Action, with English translation, issued in Japanese Patent Application No. JP 2004-303172, dated Oct. 22, 2009.

Primary Examiner — Vu Le
Assistant Examiner — Aklilu K Woldemariam
(74) Attorney, Agent, or Firm — McDermott Will & Emery LLP

(57) ABSTRACT

The inspection system arbitrarily selects from among a plurality of optical conditions to change a distribution of reflected or diffracted light component from an object being inspected. The inspection system has a one- or two-dimensional optoelectric conversion image sensor, optically acquires an image of the object by scanning a stage on which the object is mounted or scanning the image sensor, and processes the image to check for defects in the object. Under each optical condition (illumination optical system, detection optical system, scan direction, etc.) the object being inspected is imaged and, based on the brightness distribution and contrast in the detection field of the image sensor, image sensor output correction data is generated to correct the output of the image sensor.

12 Claims, 16 Drawing Sheets

U.S. PATENT DOCUMENTS

| | | | |
|---|---|---|---|
| 6,792,203 B1 * | 9/2004 | Ide et al. | 396/65 |
| 6,826,362 B2 * | 11/2004 | Matsuo | 396/104 |
| 6,928,185 B2 * | 8/2005 | Yonezawa | 382/149 |
| 2004/0240723 A1 * | 12/2004 | Sakai et al. | 382/141 |
| 2004/0262529 A1 * | 12/2004 | Yoshida et al. | 250/372 |
| 2007/0247622 A1 * | 10/2007 | Sun | 356/364 |

FOREIGN PATENT DOCUMENTS

| | | |
|---|---|---|
| JP | 2000-358160 A | 12/2000 |
| JP | 2003-098113 | 4/2003 |
| JP | 2005-147691 A | 6/2004 |

* cited by examiner

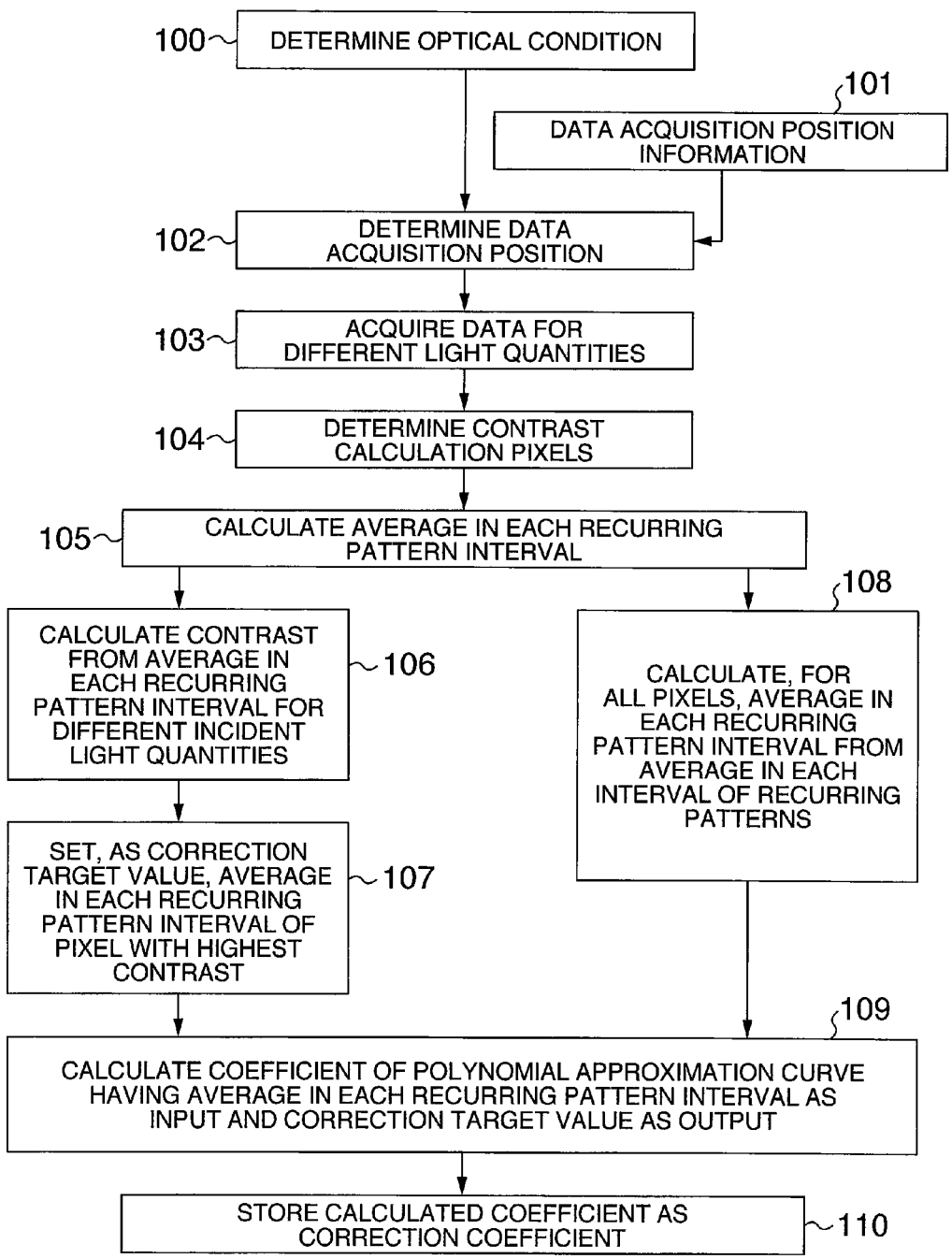

PRODUCT WAFER, OPTICAL CONDITION A; AFTER CONVENTIONAL CORRECTION

ACQUISITION OF DATA FOR DIFFERENT ILLUMINATING LIGHT QUANTITIES

CALCULATION OF CONTRAST

CALCULATION OF CORRECTION COEFFICIENT
(EXAMPLE OF SENSOR PIXEL k)

AFTER CORRECTION OF THIS METHOD

CONTRAST MEASUREMENT/CORRECTION START SCREEN

DISPLAY SCREEN FOR CONTRAST CORRECTION RESULT

INSPECTION SYSTEM AND INSPECTION METHOD

RELATED APPLICATIONS

This application is a Continuation of U.S. patent application Ser. No. 11/251,909, now U.S. Pat. No. 7,697,746, filed on Oct. 18, 2005, claiming priority of Japanese Patent Application No. 2004-303172, filed on Oct. 18, 2004, the entire contents of each of which are hereby incorporated by reference.

BACKGROUND OF THE INVENTION

The present invention relates to an inspection to detect defects (short circuits and broken circuits) and foreign particles in patterns being inspected, and more specifically to a method of correcting a sensor output particularly when a one-dimensional or two-dimensional image sensor is used as a detector.

Conventional techniques associated with image sensor shading correction include: a method which, as disclosed in JP-A-2000-358160, moves a carriage to scan a text reading window, which is fixed at a home position, over a reference white plate and, based on the white reference position thus read, generates correction data; and a method which, as disclosed in JP-A-10-224529, sets a first mode that variably magnifies a read image by changing the scan speed of the line sensor, a second mode that variably magnifies a read image by a variable magnification circuit, and a third mode that performs both a variable magnification by changing the line sensor scan speed and a variable magnification by a variable magnification circuit, and adaptively selects one of the modes according to a size of an original and a reading resolution.

SUMMARY OF THE INVENTION

In an inspection system that uses an optoelectric conversion type image sensor as a detector and which can set a plurality of optical conditions, a conventional method disclosed in JP-A-2000-358160 has a problem that, in an optical condition where reflected light or diffracted light from an object being inspected changes according to a pattern density of the object, because a brightness distribution of light detected by the detector when the sensor output correction data is generated differs from that when an inspection is made, a precise correction cannot be done in generating sensor output correction data for correcting a shading of the detector, rendering the sensor output uneven and degrading contrast where the brightness level is low (dark). Further, another conventional method disclosed in JP-A-10-224529, although it can cope with changes in optical condition and speed, cannot deal with an optical condition where the brightness distribution of detected light is different, so that the sensor output is ununiform even after the shading correction is made.

An object of the present invention is to provide an inspection system having a sensor output correction function to make uniform the sensitivity of the image sensor in a detection field and also a sensor output correction method.

To achieve the above objective, the present invention provides an inspection system which can arbitrarily select from among a plurality of optical conditions to change a distribution of components of reflected light or diffracted light from an object being inspected, which has a one-dimensional or two-dimensional optoelectric conversion image sensor, and which scans a stage mounting the object being inspected or the image sensor to optically obtain an image, processes the image and checks it for defects in the object, wherein, based on a contrast calculated from a brightness distribution in an image sensor detection field obtained by photographing the object sample for each optical condition (e.g., illumination optical system, detection optical system and scan direction), image sensor output correction data is generated to correct the image sensor output.

There are two methods for correcting an image sensor output: one is to take as a correction target value an output of a sensor pixel corresponding to a position in the field of view at which the contrast becomes maximum, and correct outputs of individual sensor pixels of the image sensor based on the correction target value; and the other involves taking as a target contrast a contrast at a position in the field of view at which the contrast is maximum and correcting outputs of individual sensor pixels of the image sensor so as to achieve the target contrast at all positions in the viewing field.

This invention can keep the contrast uniform in the viewing field of the image sensor and, by giving a correction target value from outside, improve the contrast of the detected image, thus reducing the incidence of defect overlook and false detection, which in turn provides an inspection system with so high and stable a sensitivity as to detect even minute defects. Further, by sharing the correction target value among inspection systems, it is possible to provide inspection systems whose detection sensitivities are stable and have no differences among the systems.

Other objects, features and advantages of the invention will become apparent from the following description of the embodiments of the invention taken in conjunction with the accompanying drawings.

BRIEF DESCRIPTION OF THE DRAWINGS

FIG. 3 illustrates an example of a process flow representing a sensor output correction method of this invention.

FIGS. 16A, 16B, 16C, 16D and 16E are explanatory views showing conventional sensor output correction methods.

DESCRIPTION OF THE EMBODIMENTS

Now, embodiments of this invention will be described by referring to the accompanying drawings. In the following explanation, a semiconductor wafer is taken for example.

Figure 1:
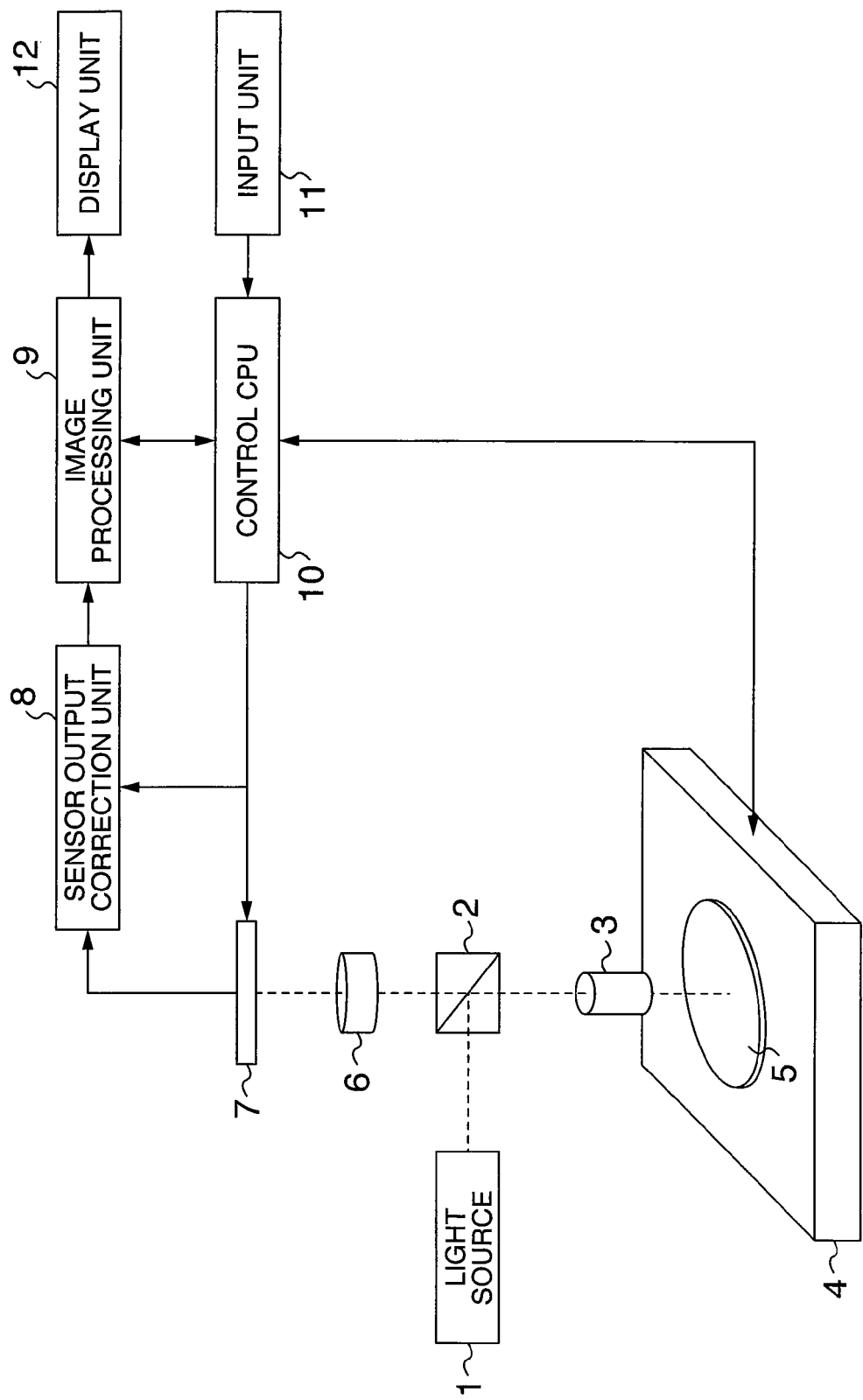
FIG. 1 is a conceptual view showing an example of an inspection system having a sensor output correction function of this invention.

FIG. 1 shows an conceptual view of an example inspection system having a sensor output correction function of this invention. In this inspection system, a beam of light from a light source 1 is radiated against a specimen 5 placed on a stage 4 through a beam splitter 2 and an objective 3. A reflected light from the specimen 5 is led through the objective 3, the beam splitter 2 and an imaging lens 6 to an image sensor 7 for detection. Between the image sensor 7 and the an image processing unit 9 there is a sensor output correction unit 8 that corrects contrast to make it uniform in the viewing field of the image sensor. Information entered from an input unit 11 and data from the image processing unit 9, the image sensor 7, the stage 4 and the sensor output correction unit 8 are controlled by a control CPU 10. Results of the image processing and the sensor output correction are displayed on a display unit 12.

If optical conditions, including a magnification factor of the objective 3, an illumination method (modified illumination such as bright-field illumination, dark-field illumination, polarization illumination and annular illumination), and a detection method (detection of diffracted light, such as polarization detection and spatial filter detection), are changed, the use in each optical condition of the sensor output correction method of this invention described later can keep the contrast in the viewing field of the image sensor uniform, making it possible to produce a satisfactory detection result with high and uniform detection sensitivity in the viewing field of the image sensor. Further, by sharing a correction target value among the inspection systems, contrast variations in the viewing field of the image sensor can be eliminated, providing an inspection system having no detection sensitivity difference between it and other inspection systems or detection sensitivity variations in the viewing field.

Figure 2:
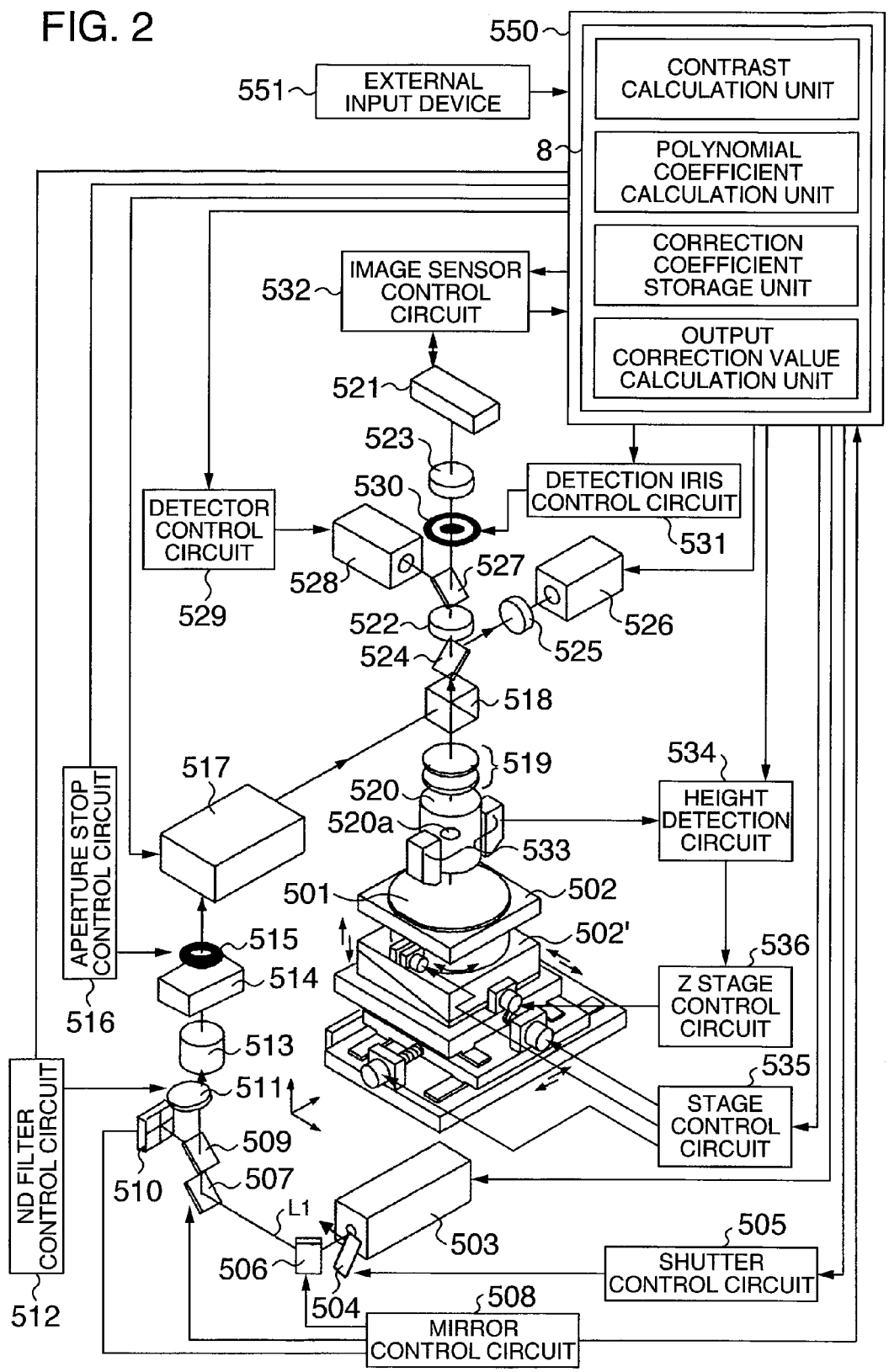
FIG. 2 illustrates a more detailed construction of the inspection system having the sensor output correction function of this invention.

FIG. 2 shows an example of a more detailed construction of the inspection system having a sensor output correction function of this invention. A stage 502 comprises X, Y, Z and θ (rotation) stages and mounts a semiconductor wafer (specimen) 501, an example pattern to be inspected. A light source 503 may be an ultraviolet or far-ultraviolet laser light source with a wavelength of, for example, 266 nm or 355 nm to illuminate the specimen 501. The ultraviolet laser light source may be constructed of, for example, a device that converts the wavelength of a solid YAG laser as by a nonlinear optical crystal into a third harmonic (355 nm) or a fourth harmonic (266 nm) of the fundamental wave. A laser light source with a wavelength of 193 nm, 195 nm or 248 nm may also be used. If available, a laser light of 100 nm or less may be used because the use of shorter wavelength will improve a resolution. The laser may be oscillated either by a continuous oscillation or a pulse oscillation. The continuous oscillation, however, is preferred because an image of the specimen 501 is detected by continuously moving the stage. The stage 502 can be controlled in the X, Y and θ directions by a stage control circuit 535. A Z stage 502' can be controlled in the Z direction by a Z stage control circuit 536.

A luminous flux L1 from the light source 503 is controlled by a shutter 504 to pass through an optical path. The shutter 504 can be moved by a shutter control circuit 505 at any desired time. An optical axis of the luminous flux L1 can be adjusted vertically and horizontally by mirrors 506, 507. The mirrors 506, 507 can be moved vertically and horizontally. A light path division mirror 509 can extract a part of the luminous flux L1 and is installed to project a reflected beam onto a division sensor 510. A mirror control circuit 508 detects a position where the light enters the division sensor 510 and, when the light entrance position shifts from the predetermined position, moves the mirrors 506, 507 to control the optical axis. An ND filter 511 that limits a light quantity controls the amount of light required for inspection. The ND filter 511 is driven by a command from an ND filter control circuit 512. A beam expander 513 expands the luminous flux to the size of a pupil 520a of an objective 520. An optical system 514 sets a range of illumination of the expanded flux on the specimen 501. An aperture stop 515 is installed at a position conjugate with the pupil 520a of the objective 520 to limit the NA entering the pupil 520a and is driven by a command from an aperture stop control circuit 516. The luminous flux passes through a coherence reduction optical system 517 and is led by a split prism 518 to the objective 520. The coherence reduction optical system 517 reduces the coherence of the laser beam projected from the light source 503. The coherence reduction optical system 517 need only be able to reduce the time coherence or spatial coherence and may, for example, be constructed of a mechanism that scans the laser beam from the light source 503 over the pupil of the objective 520.

The split prism 518 is constructed of a polarization beam splitter and reflects a beam from the light source 503 so that the reflected beam passes through the objective 520 onto the specimen 501 for bright-field illumination. With the split prism 518 constructed of the polarization beam splitter, the beam is reflected when the polarization direction of the beam is parallel to the reflection surface and passes through the reflection surface when the polarization direction is perpendicular. Thus, since the laser beam of the light source is a polarized laser beam by nature, the laser beam can be totally reflected by the split prism 518. A polarization device group 519 controls the polarization direction of the luminous beam and reflected light to adjust a polarization ratio of the luminous beam so that the reflected light will not reach the image sensor 521 as brightness variations caused by different pattern shapes and densities. The polarization device group 519 is constructed of a half wave plate and a quarter wave plate. The half wave plate and the quarter wave plate are controlled about the optical axis to set their rotary angles to control the polarization state of the reflected light, i.e., a diffracted light from a circuit pattern formed on the specimen 501. For example, the reflected light can be detected by the image sensor 521 with a 0-th diffracted light attenuated but higher orders of the diffracted light almost not attenuated. As a result, the pattern contrast dramatically improves assuring a stable detection sensitivity.

The illuminating beam is radiated through the objective 520 against the specimen 501 and the reflected light is extracted by the objective 520. The reflected light passes through an imaging lens 522 and a relay lens 523 to form an image on the image sensor 521. The image sensor 521 has a pixel dimension of about 0.05 μm to 0.3 μm as measured on the specimen and produces a grayscale image signal representing a brightness (gray level) of the reflected light from the specimen 501, one example of a pattern being inspected. The objective 520 may be a refraction type lens or a reflection type lens. In the optical path between the split prism 518 and the imaging lens 522 there is provided a beam splitter 524 which sends its reflected light through a lens 525 into a detector 526, such as a CCD camera, to enable an observation of the pupil 520a of the objective 520. The beam splitter 524 is so set that its reflection is about 5% and thus has an optical characteristic that most of its light is a transmitting light, minimizing its adverse effect on the light quantity required for inspection. Further, a mirror 527 is inserted in the optical path between the imaging lens 522 and the relay lens 523. The luminous flux reflected by the mirror 527 is led to a detector 528, such as a CCD camera, which is provided at an image forming position of the imaging lens 522. Thus, an image of the specimen 501 can be observed by the detector 528. The picture shooting timing of the detector 528 can be controlled by a detector control circuit 529. This mirror 527 can be inserted into or removed from the optical path by a method not shown. During inspection this mirror 527 is removed to prevent the light quantity required for inspection from being affected. At the image forming position of the imaging lens 522 a detection iris 530 is installed. The detection iris 530 can, according to a detection iris control circuit 531, control a diameter of a detection luminous flux. The image sensor 521 can be controlled in its drive speed and timing by an image sensor control circuit 532.

An auto focusing system 533 to keep the surface of the specimen 501 aligned with the focal point position of the objective 520 at all times is installed near the objective 520. Based on an output from the auto focusing system 533, a height detection circuit 534 measures the height of the specimen 501 and inputs a height difference into a Z stage control circuit 536 which then controls a Z stage 502' to adjust the height of the specimen 501. A system control circuit 550 performs a control on all the aforementioned control circuits and processing on a signal from the image sensor 521, and incorporates a sensor output correction unit 8 that makes the brightness distribution or contrast uniform in the viewing field of the image sensor. The sensor output correction unit 8 includes a contrast calculation unit, a polynomial coefficient calculation unit, a correction coefficient storage unit and an output correction value calculation unit. The contrast calculation unit, as described later with reference to FIG. 5, has a function to calculate a contrast at least near the ends or center of the viewing field of the image sensor. The polynomial coefficient calculation unit, as described later by referring to FIG. 6 or FIG. 10, has a function to calculate a coefficient of an output correction polynomial for each sensor pixel of the image sensor. The correction coefficient storage unit stores the coefficient of the output correction polynomial calculated by the polynomial coefficient calculation unit. The output correction value calculation unit has a function to calculate a correction value for an average output value of each sensor pixel of the image sensor for each light quantity during a sensor pixel output correction mode so that the contrast matches a target contrast.

These optical systems are constructed on an optical stand not shown in such a way that the light source and the optical systems, such as the illumination optical system, the detection optical system and the image sensor, are built as one integral system. The optical stand may, for example, be formed like a gate and mounted on the same flat table on which the stage 502 is installed so that it does not interfere with a range of movement of the stage 502. This arrangement ensures a stable detection even when the system is subjected to temperature changes and vibrations.

In the construction described above, an ultraviolet beam (e.g., ultraviolet laser beam) L1 projected from the light source 503 is reflected by the mirrors 506, 507, passes through the ND filter 511 that limits the light quantity, is expanded by the beam expander 513, enters the objective 520 through the coherence reduction optical system 517, split prism 518 and polarization device group 519, and is radiated against the specimen (semiconductor wafer) 501. That is, the ultraviolet beam is collected on the pupil 520a of the objective 520 and then Koehler-illuminated onto the specimen 501. The reflected light from the specimen 501 is detected by the image sensor 521 through the objective 520, polarization device group 519, split prism 518, imaging lens 522 and relay lens 523 arranged vertically above the specimen 501. During inspection, the stage 502 is scanned to move the specimen 501 at a constant speed. At the same time the auto focusing system 533 continuously detects the Z-direction position of the surface of the specimen 501 being inspected and controls the Z stage 502' in the Z direction so that the distance between the specimen surface and the objective 520 is always constant. The image sensor 521 detects with high precision brightness information (grayscale image signal) of the target pattern formed on the specimen 501. The output from the image sensor 521 is processed by the system control circuit 550 that incorporates the sensor output correction unit 8.

FIG. 3 shows one embodiment of the process flow of the image sensor output correction method according to this invention.

First, at step 100 optical conditions, including illumination condition, detection condition and magnification factor, under which to inspect a product wafer with an uneven surface, such as a pattern, are determined. Next, at step 102, to determine at which coordinate on the object data for sensor output correction is to be picked up, data extraction position information 101, which was given as parameter by an external input means such as GUI (graphical user interface), is retrieved to decide the data extraction position.

Figure 4A:
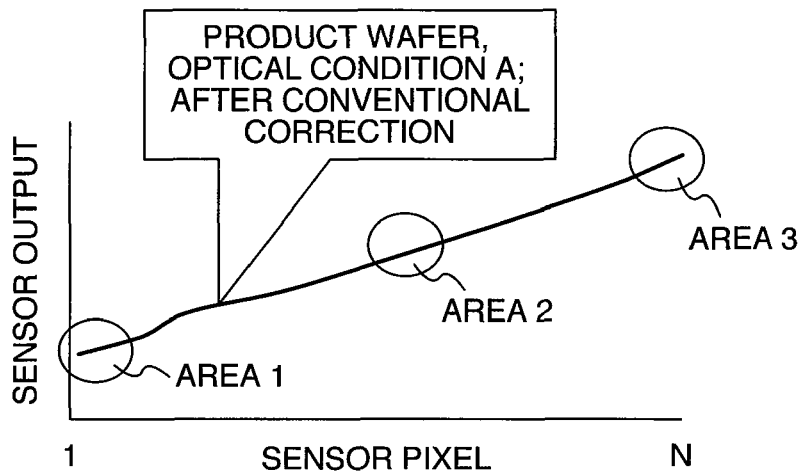
FIGS. 4A and 4B are explanatory views showing how data is picked up from a product wafer.

The calculation of the correction coefficient described later requires the brightness distribution for all sensor pixels in the viewing field of the image sensor. Since the brightness distribution interpolation equation for all sensor pixels can be calculated by using only those data in area 1, area 2 and area 3 near the ends and center of the image sensor viewing field shown in FIG. 4A as long as no special patterns exist in the area 1, area 2 and area 3, the data extraction position on the product wafer may be determined automatically or semi-automatically by using design data and coordinate data of the product wafer. It is also possible to add a function of deciding how much valid data there is in the area 1, area 2 and area 3 that can be used in calculating the brightness distribution interpolation equation. Further, if effective data for calculating the brightness distribution interpolation equation exits only at one or two locations in the viewing field of the image sensor, the photographing position may be changed to shoot two or three pictures of different areas so that effective data for calculating the brightness distribution interpolation equation lies in the area 1, area 2 and area 3 and then the photographed data may be combined to calculate the interpolation equation of the brightness distribution in the viewing field of the image sensor. Alternatively, the interpolation equation of the brightness distribution in the image sensor viewing field may be calculated directly from the two or three area picture data that were shot in succession. If there are two or more data extraction positions on the product wafer, the plurality of data may be averaged and, from this average value, the brightness distribution interpolation equation may be calculated. It is also possible to divide the product wafer into a plurality of inspection areas and calculate the brightness distribution interpolation equation for each inspection area. Because the accuracy of the interpolation equation improves as the number of areas for calculating the brightness distribution interpolation equation increases, a plurality of inspection areas may be provided in addition to those areas near the ends or center of the image sensor viewing field.

Figure 4B:
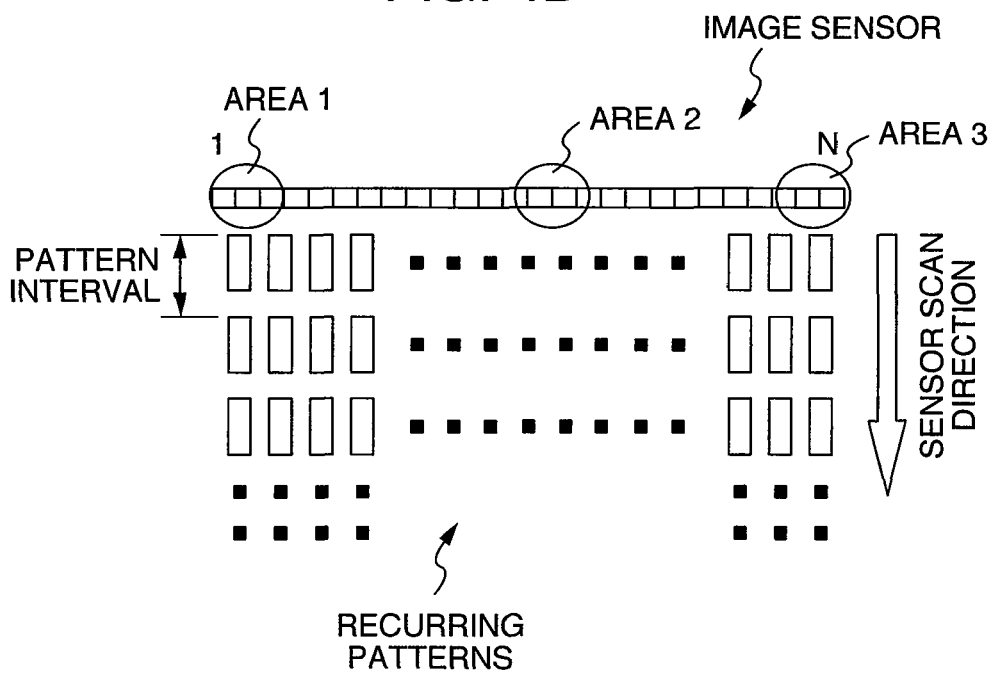

FIG. 4B is a schematic diagram showing how the brightness distribution in the viewing field of the image sensor is measured for all sensor pixels. The inspection areas on the product wafer are illuminated with light, repetitive patterns formed in the inspection areas are scanned by the image sensor, and an average of the sensor output is taken for each pattern interval in the scan direction of the sensor pixels.

Then the processing proceeds to step 103 where the illuminating light quantity is changed stepwise to acquire data for different incident light quantities to generate sensor output correction data. At this time, if the detector uses a sensor whose scan direction is bidirectional, like a TDI (time delay & integration) image sensor, data for both directions, forward and backward, are acquired. Next at step 104, contrast calculation sensor pixels to calculate contrast are determined. The contrast calculation sensor pixels are selected from among the sensor pixels that can be used for calculating the brightness distribution interpolation equation.

Figure 5A:
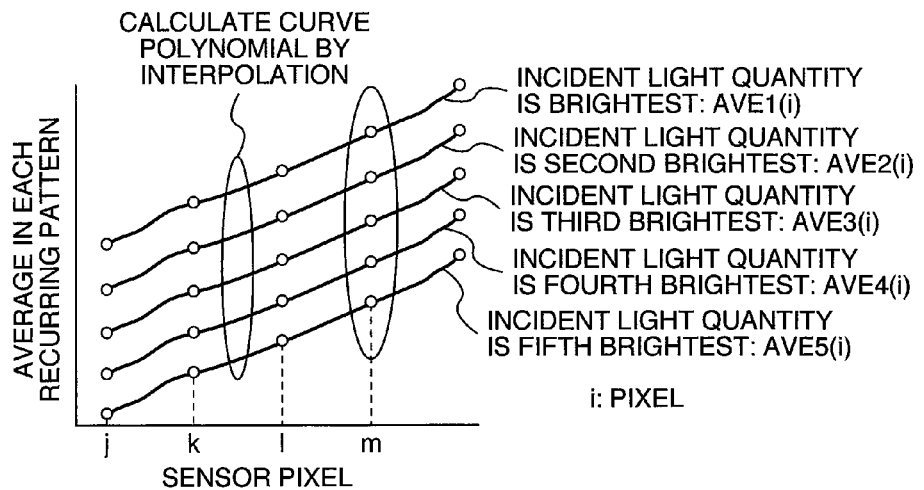
FIGS. 5A and 5B are explanatory views showing how data is obtained by brightness level and how contrast is calculated.
Figure 6A:
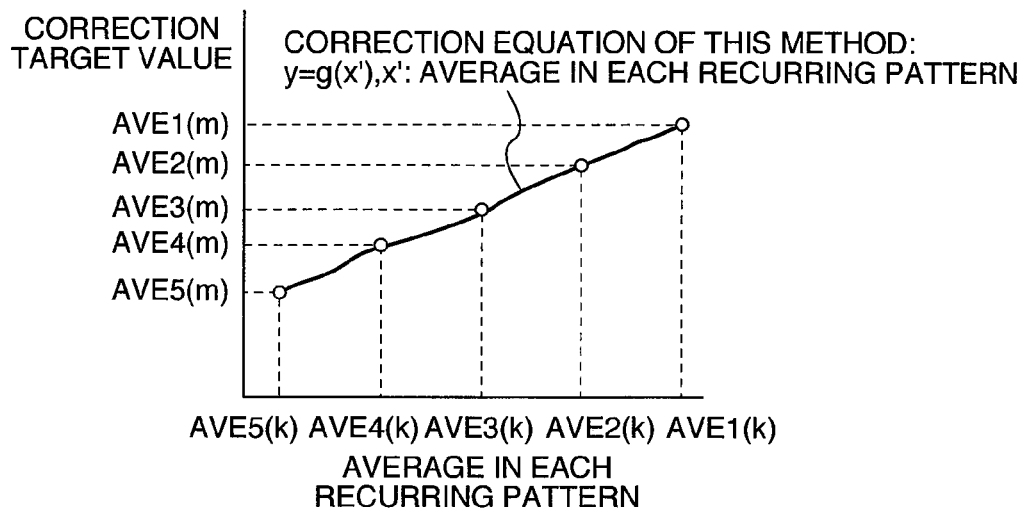
FIGS. 6A and 6B illustrate one example of a polynomial approximation curve to correct an output from each sensor pixel.

Next, in step 105, to acquire such original data for use in the calculation of contrast for each sensor pixel as will not be affected by the pattern shape of the product wafer during the contrast calculation, an output average of contrast calculation sensor pixels in each interval of recurring patterns is calculated for different incident light quantity data as shown in FIG. 5A (the "output average in each interval of recurring patterns" is simply referred to as an "output average"). In step 108, from the calculated output average for the plurality of sensor pixels, a curve polynomial is determined by interpolation and, by using this interpolated equation, an output average for all sensor pixels is calculated. Here, the degree of curve polynomial needs only to be optimized according to the product wafer as the object to be inspected and to the output characteristic and optical conditions of the image sensor used.

Figure 5B:
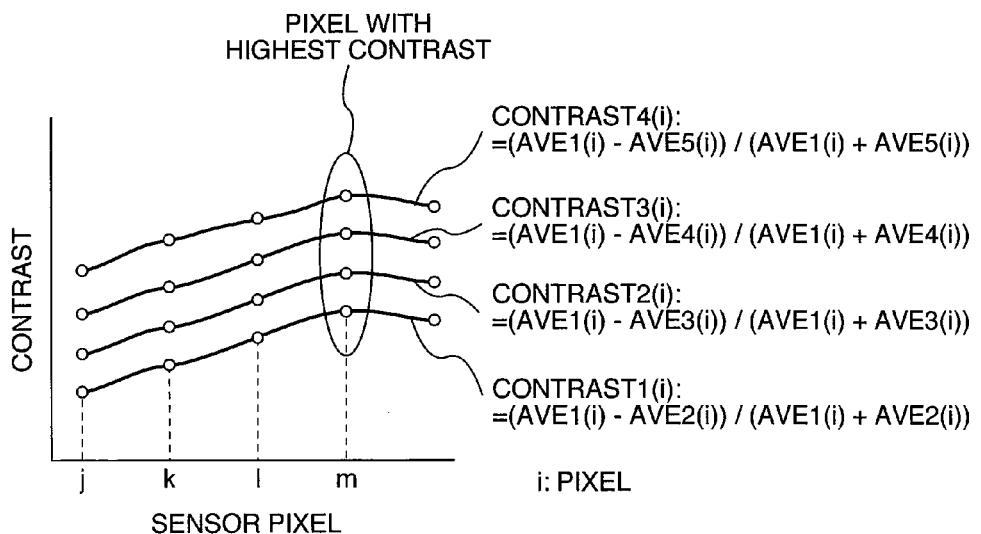

In step 106, an output average when the incident light quantity is highest and an output average when the incident light quantity is otherwise are used to calculate the contrast for each contrast calculation sensor pixel, as shown in FIG. 5B. When five stages of incident light quantity data are acquired as shown in FIG. 5A, the contrast (contrast $1(i)$, i: sensor pixel) between the output average when the incident light quantity is brightest ($AVE1(i)$, is sensor pixel) and the output average when the incident light quantity is second brightest ($AVE2(i)$, i: sensor pixel) is given by $(AVE1(i)-AVE2(i))/(AVE1(i)+AVE2(i))$, as shown in FIG. 5B. In the explanation that follows, i is taken to be a sensor pixel number. The contrast $2(i)$ between the output average $AVE1(i)$ when the incident light quantity is brightest and the output average $AVE3(i)$ when the incident light quantity is third brightest is given by $(AVE1(i)-AVE3(i))/(AVE1(i)+AVE3(i))$; the contrast $3(i)$ between the output average $AVE1(i)$ when the incident light quantity is brightest and the output average $AVE4(i)$ when the incident light quantity is fourth brightest is given by $(AVE1(i)-AVE4(i))/(AVE1(i)+AVE4(i))$; and the contrast $4(i)$ between the output average $AVE1(i)$ when the incident light quantity is brightest and the output average $AVE5(i)$ when the incident light quantity is fifth brightest is given by $(AVE1(i)-AVE5(i))/(AVE1(i)+AVE5(i))$.

Next, in step 107, the output average for each incident light quantity in the sensor pixel with the largest calculated contrast is taken as a correction target value. Step 109 uses the result of step 107 and the result of step 108 to calculate a coefficient of a polynomial approximation curve (y=g(x'), x': output average in each recurring pattern) that, for all sensor pixels, has in the input (abscissa) an output average in each interval of the recurring patterns and also has a correction target value in the output (ordinate). In the example shown in FIG. 5, since the sensor pixel with the highest contrast is a sensor pixel m, a polynomial approximation curve y=g(x') for a sensor pixel k, for example, corrects $AVE1(k)$ into $AVE1(m)$, $AVE2(k)$ into $AVE2(m)$, $AVE3(k)$ into $AVE3(m)$, $AVE4(k)$ into $AVE4(m)$, and $AVE5(k)$ into $AVE5(m)$. Similarly, a polynomial approximation curve for a sensor pixel l corrects $AVE1(l)$ into $AVE1(m)$, $AVE2(l)$ into $AVE2(m)$, $AVE3(l)$ into $AVE3(m)$, $AVE4(l)$ into $AVE4(m)$ and $AVE5(l)$ into $AVE5(m)$.

Figure 6B:
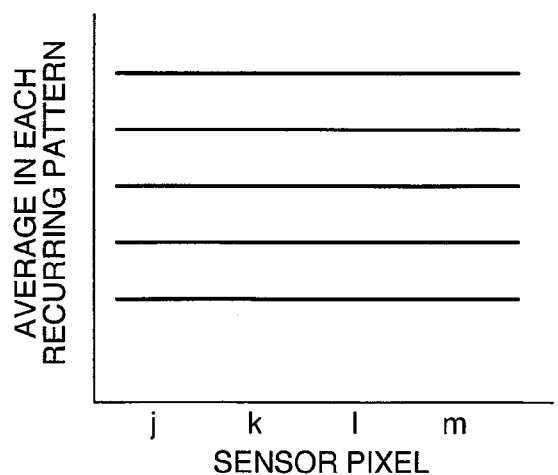
Figure 7:
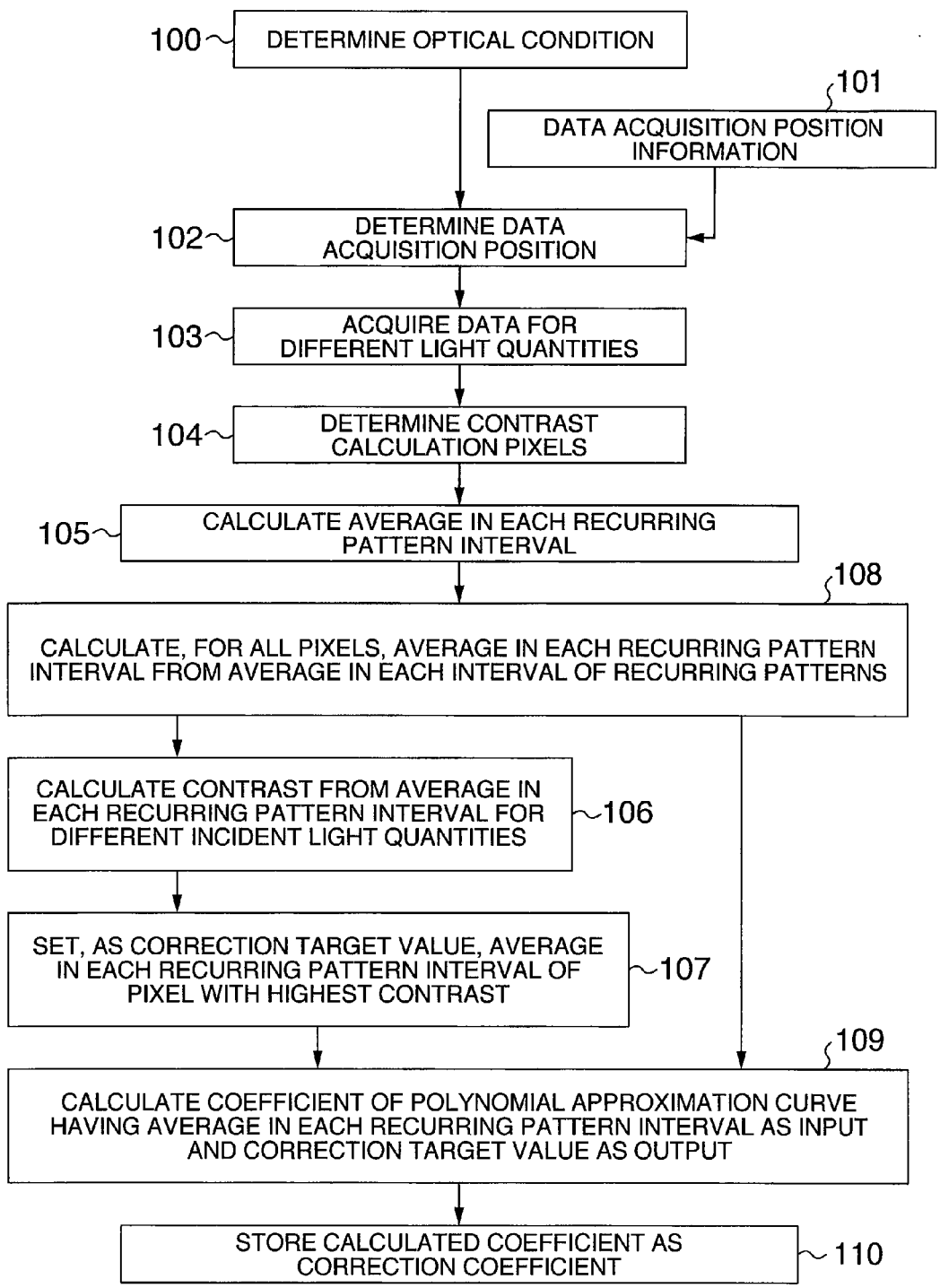
FIG. 7 shows another example of a process flow of the sensor output correction method of this invention.

Step 110 stores the calculated coefficient as a correction coefficient. The polynomial approximation curve (y=g(x'), x': output average in each recurring pattern) is calculated for each sensor pixel of the image sensor. Using the polynomial approximation curve thus calculated, the output of each sensor pixel is corrected, rendering the sensitivity characteristic of the image sensor uniform among the sensor pixels, as shown in FIG. 6B.

Figure 8:
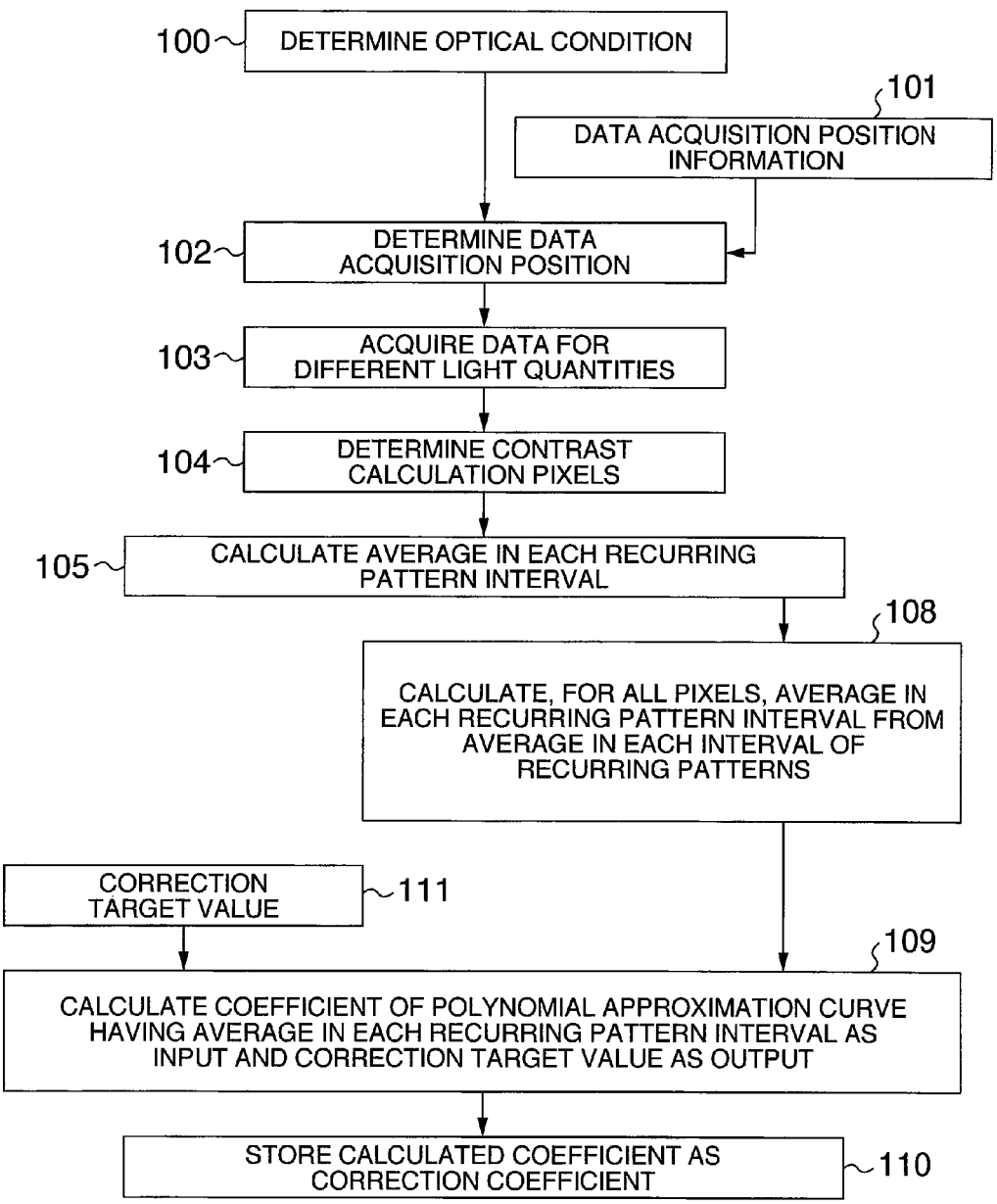
FIG. 8 shows still another example of a process flow of the sensor output correction method of this invention.

The polynomial approximation curve y=g(x') is calculated by interpolation such as the method of least squares, and the degree of the polynomial needs only to be optimized according to the product wafer as the object being inspected and to the output characteristic and optical condition of the image sensor used. To enable a more detailed extraction of the contrast distribution in the viewing field when calculating the contrast, step 108 may be executed before step 106 and the output average for all sensor pixels calculated by step 108 may be used to calculate the contrast in step 106 from the output average when the incident light quantity is brightest and the output average when the incident light quantity is otherwise, in order to allow the contrast to be calculated at uniformly distributed positions in the viewing field. Further, as shown in FIG. 8, instead of using the method that determines the correction target value by step 106 and 107, it is possible to give the correction target value 111 as a parameter from an external input means such as GUI. The correction target value 111 may vary from one sensor pixel to another or may be the same for all sensor pixels. By differentiating the correction target value among different sensor pixels, the sensitivity characteristic of the image sensor can be finely adjusted. Further, it is also possible to give as the correction target value 111 a corrected value for each sensor pixel from another inspection system to eliminate contrast differences for each sensor pixel among a plurality of inspection systems thereby making the detection sensitivities of different inspection systems equal at each position.

Figure 9:
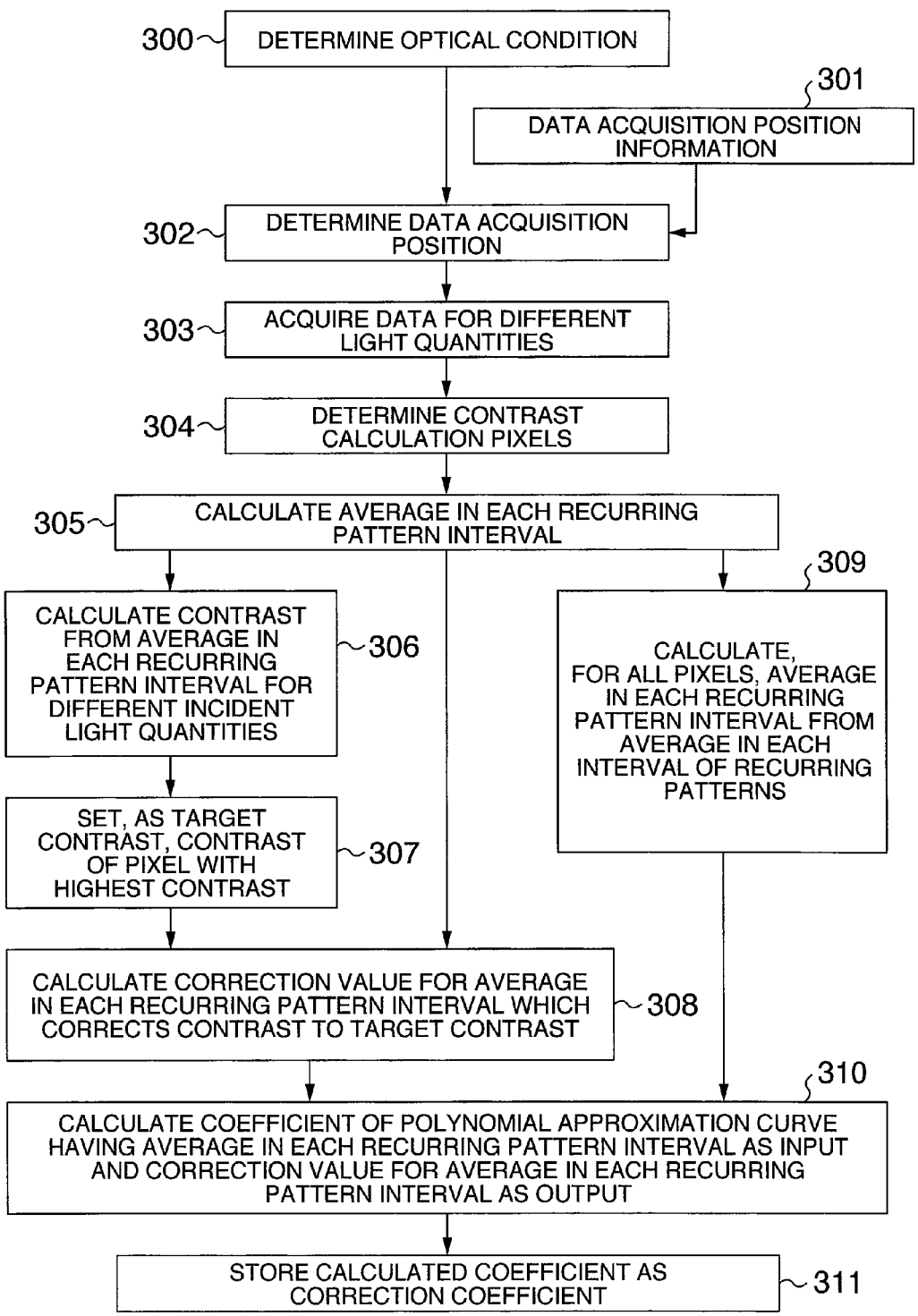
FIG. 9 shows yet another example of a process flow of the sensor output correction method of this invention.

FIG. 9 shows another example of process flow of the image sensor output correction method according to this invention. Step 300 to step 305 in FIG. 9 are identical with step 100 to step 105 of FIG. 3, and therefore the same explanations are omitted. The processing in step 309 is similar to step 108 of FIG. 3 that was explained using FIG. 5A. The processing at step 306 is similar to step 106 that was explained using FIG. 5B. That is, when five stages of incident light quantity data are acquired, as shown in FIG. 5A, the processing at step 306 produces the following data of contrast $1(i)$, contrast $2(i)$, contrast $3(i)$ and contrast $4(i)$, as shown in FIG. 5B, i representing a sensor pixel number.

Contrast $1(i)$: $(AVE1(i)-AVE2(i))/(AVE1(i)+AVE2(i))$
Contrast $2(i)$: $(AVE1(i)-AVE3(i))/(AVE1(i)+AVE3(i))$
Contrast $3(i)$: $(AVE1(i)-AVE4(i))/(AVE1(i)+AVE4(i))$
Contrast $4(i)$: $(AVE1(i)-AVE5(i))/(AVE1(i)+AVE5(i))$ Next, at step 307, the contrast for each incident light quantity of a sensor pixel with the maximum calculated contrast is taken as the target contrast (target 1-4). At the next step 308, a correction value for the output average that makes a contrast the target contrast is calculated.

Figure 10:
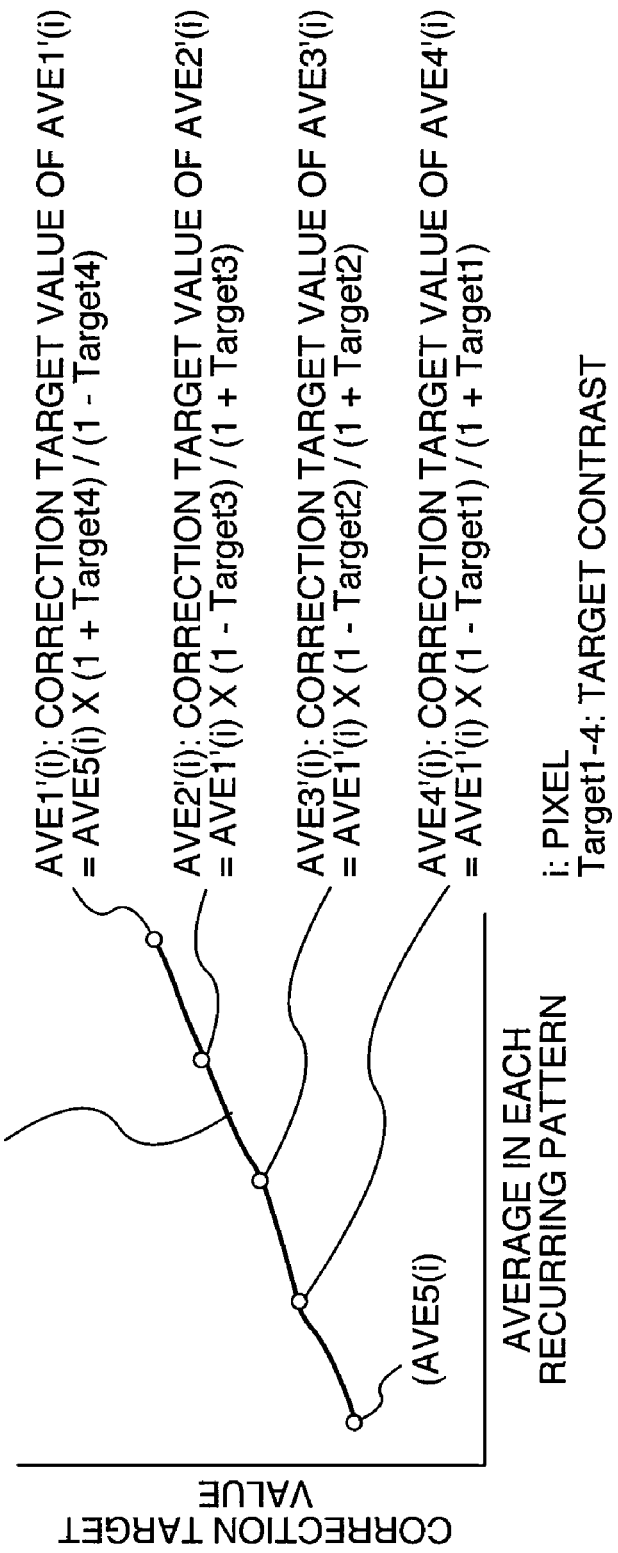
FIG. 10 illustrates another example of a polynomial approximation curve to correct an output from each sensor pixel.

When five stages of incident light quantity data are acquired as shown in FIG. 5A, the output average AVE5($i$) when the incident light quantity is fifth brightest remains unchanged after the correction, as shown in FIG. 10. The correction target value AVE1'(i) for the output average AVE1($i$) when the incident light quantity is brightest, the correction target value AVE2'(i) for the output average AVE2($i$) when the incident light quantity is second brightest, the correction target value AVE3'(i) for the output average AVE3($i$) when the incident light quantity is third brightest, and the correction target value AVE4'(i) for the output average AVE4($i$) when the incident light quantity is the fourth brightest, are given as follows. i represents a sensor pixel number.

AVE1'(i): AVE5($i$)×(1+Target4)/(1−Target4)
AVE2'(i): AVE1'(i)×(1−Target3)/(1+Target3)
AVE3'(i): AVE1'(i)×(1−Target2)/(1+Target2)
AVE4'(i): AVE1'(i)×(1−Target1)/(1+Target1)

Each of the target contrasts is the contrast value in the sensor pixel with the highest of all contrasts. Target1 is a contrast value in contrast1($i$); Target2 is a contrast value in contrast2($i$); Target3 is a contrast value in contrast3($i$); and Target4 is a contrast value in contrast4($i$). In the example of FIG. 5, since the sensor pixel with the highest of all calculated contrasts is m, Target1 is contrast1($m$), Target2 is contrast2($m$), Target3 is contrast3($m$), and Target4 is contrast4($m$).

After the correction target value has been calculated in step 308, a coefficient is calculated of a polynomial approximation curve (y=g(x'), x': output average in each recurring pattern) which, as shown in FIG. 10, has in its input (abscissa) for each sensor pixel an output average of all sensor pixels obtained by calculating the curve polynomial using a plurality of output averages and which has a correction target value in its output (ordinate) (step 310). The calculated coefficient is then stored as a correction coefficient (step 311). The polynomial approximation curve is calculated by interpolation such as the method of least squares and the degree of the polynomial needs only to be optimized according to the product wafer as the inspection object and to the output characteristic and optical conditions of the image sensor used.

Figure 11:
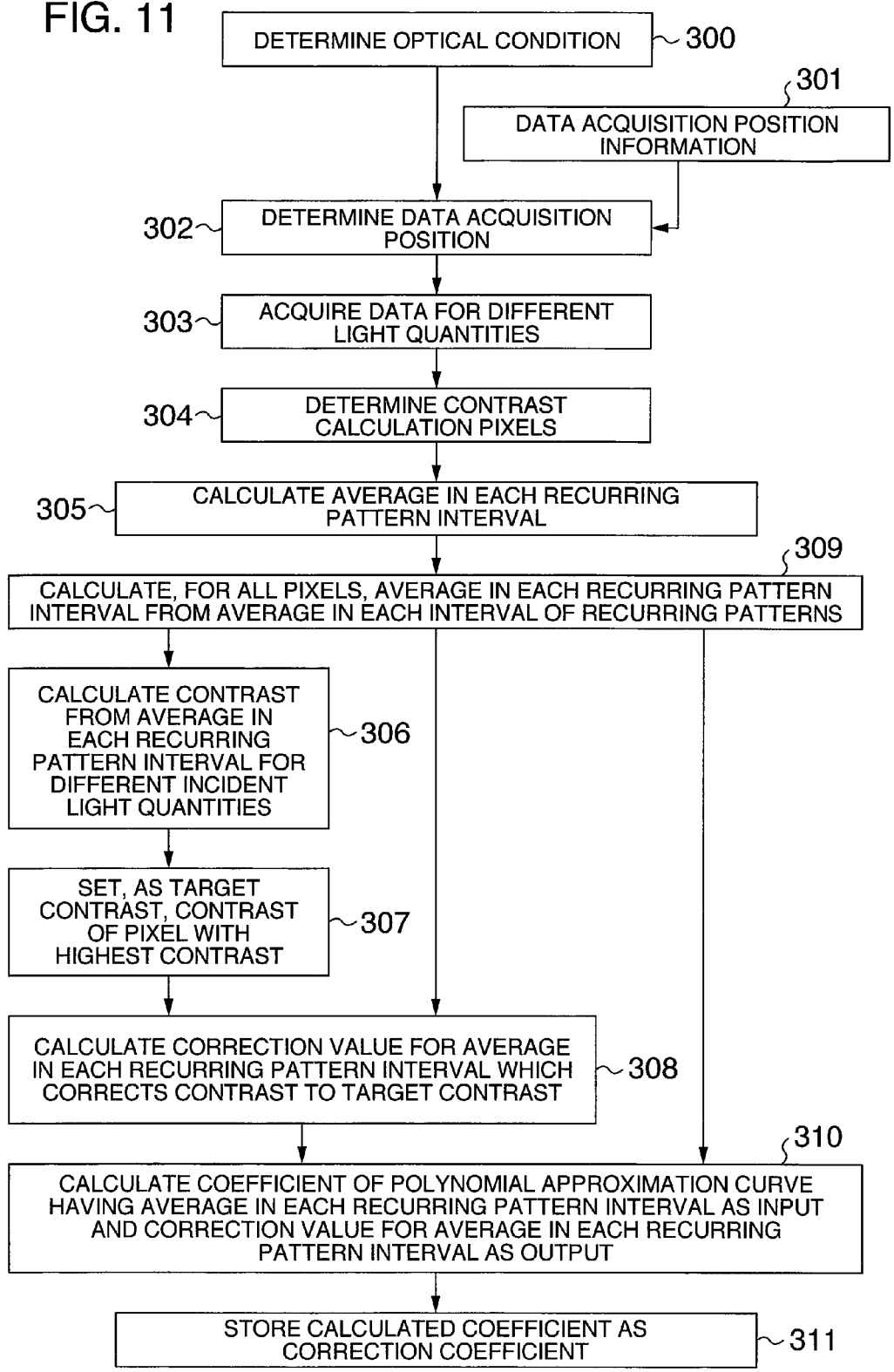
FIG. 11 shows another example of a process flow of the sensor output correction method of this invention.
Figure 12:
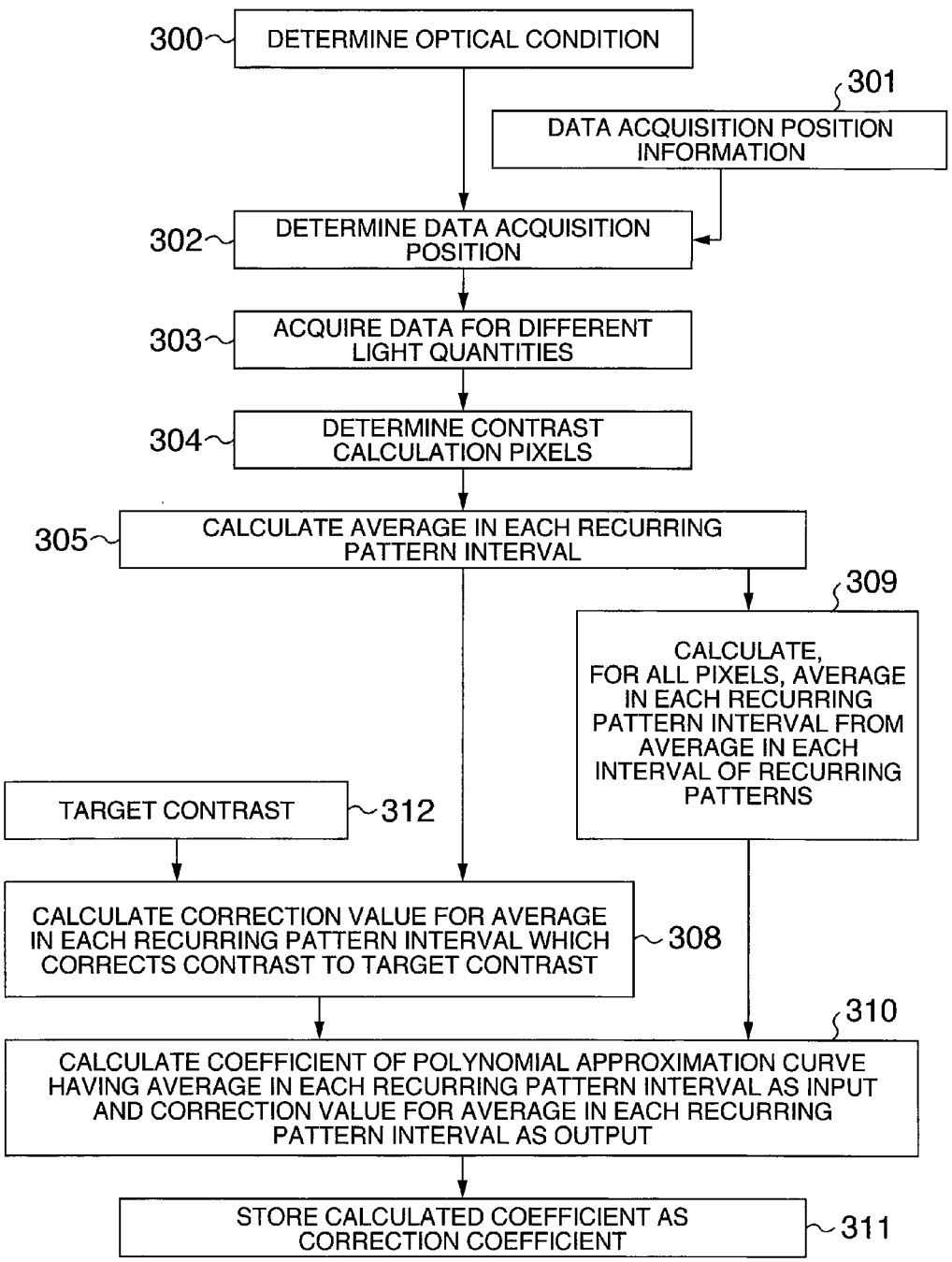
FIG. 12 shows a further example of a process flow of the sensor output correction method of this invention.
Figure 13:
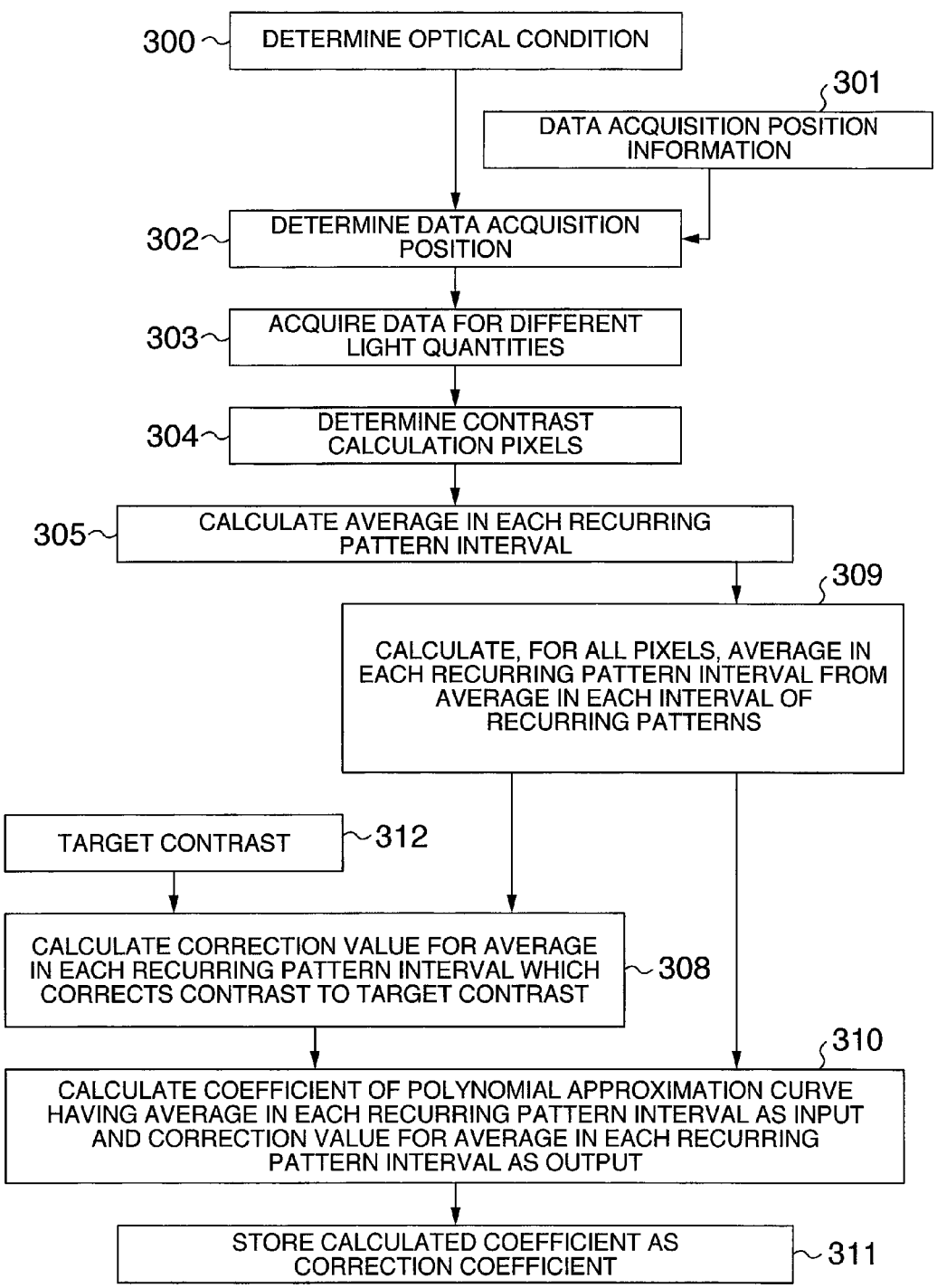
FIG. 13 shows a further example of a process flow of the sensor output correction method of this invention.

To allow for contrast calculations at uniformly distributed positions in the viewing field so that a more detailed extraction of the contrast distribution in the viewing field can be made when calculating the contrast, it is possible, as shown in FIG. 11, to calculate an output average for all sensor pixels by interpolating the curve polynomial using a plurality of output averages (step 309), to calculate the contrast from the output average obtained when the incident light quantity is brightest and the output average in each pattern interval obtained when the incident light quantity is otherwise (step 306), and to calculate a correction value for the output average that makes the contrast a target contrast (step 308). As shown in FIG. 12, it is also possible to give the correction target value 312 as a parameter from an external input means such as GUI. The correction target value 312 may vary from one sensor pixel to another or may be the same value for all sensor pixels. Further, it is also possible to give as the correction target value 312 a corrected value for each sensor pixel from another inspection system to eliminate contrast differences for each sensor pixel among a plurality of inspection systems thereby making the detection sensitivities of different inspection systems equal at each position. Further, as shown in FIG. 13, the correction target value 312 may be given as a parameter by an external input means such as GUI and, when calculating a correction value for the output average that makes the contrast a target contrast in step 308, the output average for all sensor pixels that was calculated in step 309 by interpolating the curve polynomial using a plurality of output averages may be used.

Figure 14:
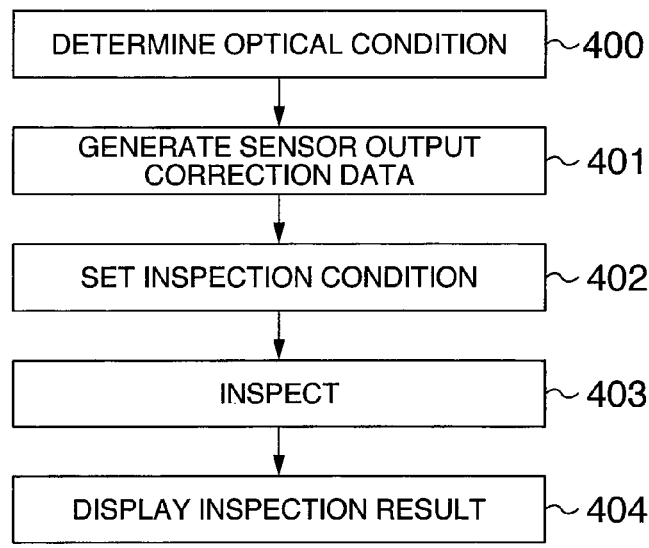
FIG. 14 shows an example of an inspection flow of the inspection system of this invention.

FIG. 14 shows one example of process flow of the inspection system according to this invention. In the inspection system capable of selecting from among a plurality of optical conditions, first at step 400 optical conditions, including illumination condition, detection condition and magnification factor, to inspect a product wafer with an uneven surface such as pattern are determined. Next, at step 401 sensor output correction data is generated by the method of FIG. 3 to FIG. 13 using a product wafer so that the contrast is uniform in the viewing field. Next, when starting the inspection, step 402 sets the parameter for image processing and the inspection conditions such as inspection range and then step 403 performs the inspection. The result of inspection is displayed by step 404.

Figure 15:
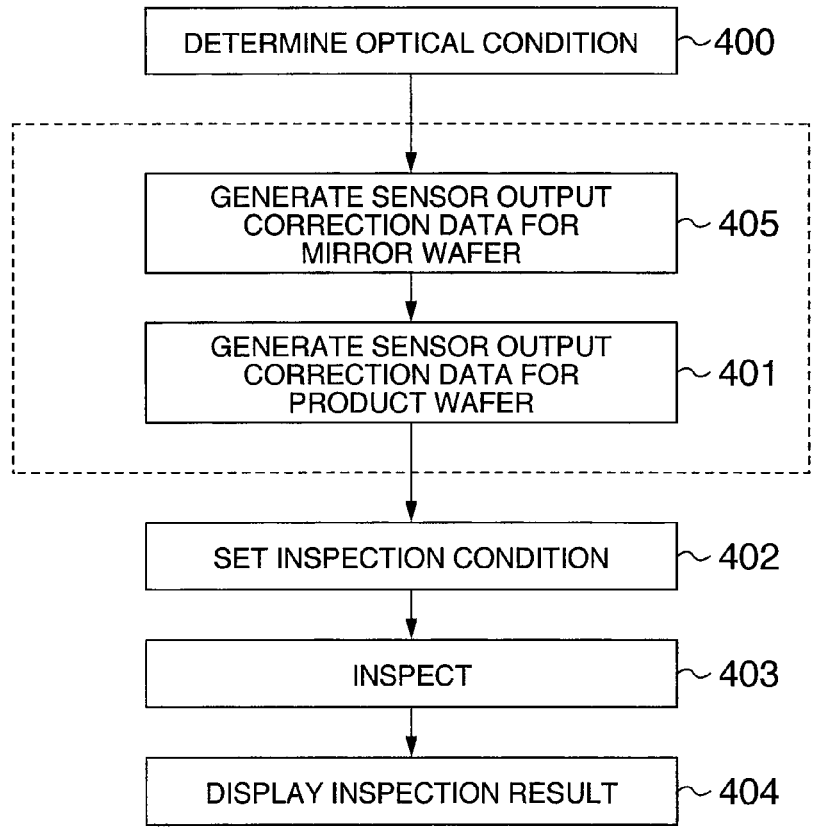
FIG. 15 shows another example of an inspection flow of the inspection system of this invention.

FIG. 15 shows another example of process flow of the inspection system according to this invention. First in step 400, optical conditions, including illumination condition, detection condition and magnification factor, to inspect a product wafer with an uneven surface such as pattern are determined. Then, at step 405, by using a mirror wafer with few undulations and no variations in reflection light distribution in the viewing field of the image sensor, a plurality of pieces of data are acquired with the incident light quantity as a parameter, as shown in FIG. 16A. Then, a first-degree or a polynomial correction curve which has a sensor output in abscissa and a corrected output in ordinate is determined for each sensor pixel, as shown in FIG. 16B. Using this correction equation (y1=f(x), x is a sensor output), sensor output correction data is generated for each sensor pixel so that the outputs for all sensor pixels take the same values when the incident light quantity is the same, as shown in FIG. 16C.

While the mirror wafer that was used to generate the sensor output correction data can correct the sensor output to be flat, if, under the optical conditions that change reflected and diffracted light components from a specimen, there is a pattern as in a product wafer and variations in the pattern density exist in the sensor viewing field, then the mirror wafer and the product wafer have different power or brightness distributions of the detection beam, making it impossible to correct the sensor output, as shown in FIG. 16D, and rendering the contrast in the sensor viewing field ununiform, as shown in FIG. 16E. To deal with this problem, the generation of sensor output correction data is performed in two steps. The additional or second step 401 of FIG. 15 involves using a product wafer, a real object to be inspected, and generating the sensor output correction data in a manner shown in FIG. 3 to FIG. 13 so that the contrast in the viewing field is uniform. When the inspection is started next, inspection conditions such as a parameter for image processing and an inspection range may be set in step 402 and then the inspection performed in step 403. The result of the inspection may be displayed in step 404.

For an inspection area or non-inspection area with no or small undulations, it is possible to calculate a correction value to correct the image sensor output distribution to be flat, as in the conventional method. The inspection of an object area with small undulations may be performed by correcting the sensor output with the calculated correction value. But for an inspection of an object area with large undulations, a correction coefficient of this invention that makes the contrast uniform in the image sensor viewing field or corrects the contrast to a target value may be re-calculated. Whether the area of a wafer to be inspected has small or large undulations can be decided by referring to the wafer coordinates, so the inspection may be done by switching between two correction coefficients according to the coordinate information.

Figure 17A:
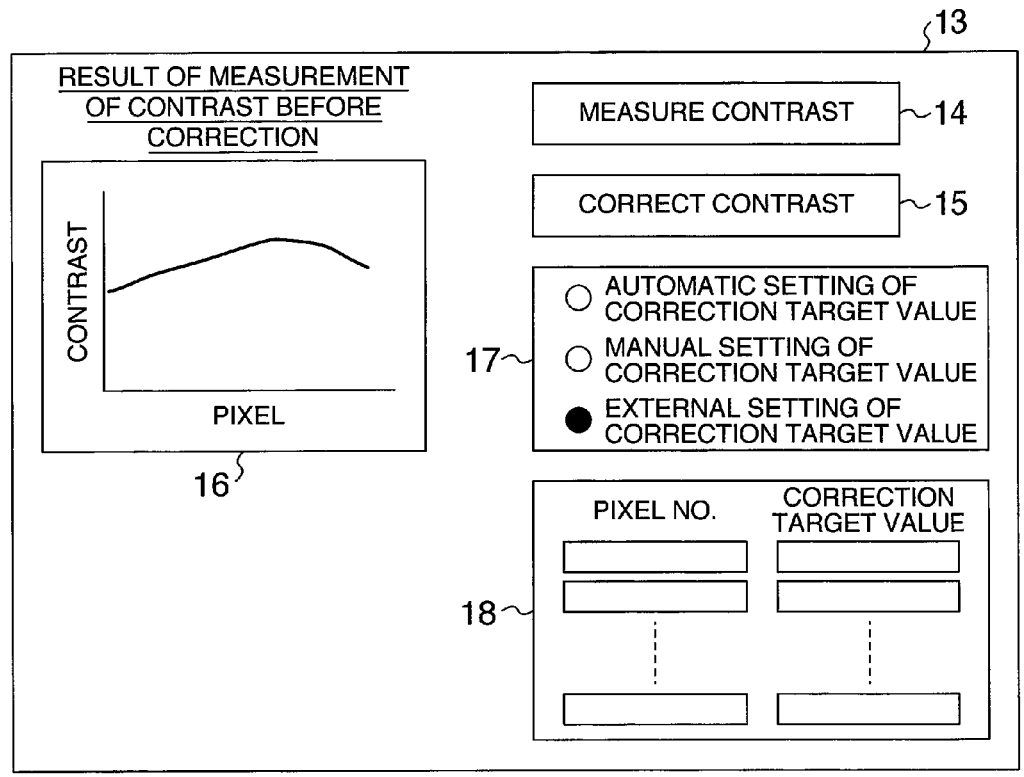
FIGS. 17A and 17B show examples of displayed images in the inspection system of this invention.
Figure 17B:
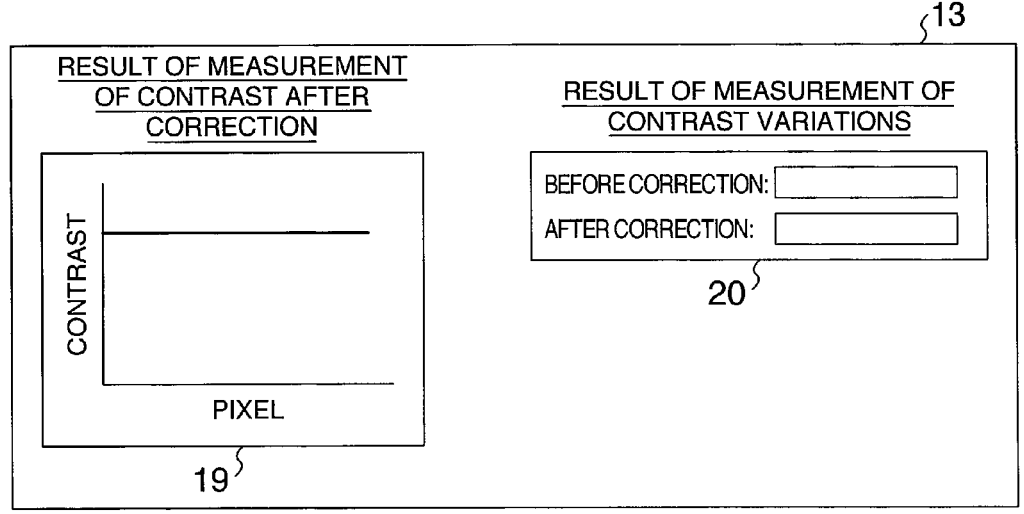

FIGS. 17A and 17B show example display screens of the inspection system of this invention. FIG. 17A is a display screen 13, such as GUI, that can be used for input and display. When one wishes to measure a contrast, he or she depresses a contrast measurement button 14 to initiate a contrast measurement and have a result of contrast measurement 16 displayed. When the contrast is corrected, a desired correction target value setting method is selected using a correction target value selection button 17. To set a correction target value manually, one is required to set a correction target value in a correction target value setting screen 18 and press a contrast correction button 15. This causes a contrast correction coefficient to be calculated and the contrast correction result to be displayed as shown in FIG. 17B. The contrast correction result display screen shows a contrast measurement result 19 after correction, and a result of measurement of contrast variations in the viewing field before and after the correction. This allows the user to easily recognize the effect of the contrast correction. When displaying the contrast measurement and the contrast correction result, the brightness distribution in the sensor viewing field may also be displayed at the same time. It is also possible to display a screen in which to set positions where contrast measurements are to be made.

The use of the sensor output correction method of this invention can keep the contrast in the viewing field of the image sensor 521 uniform and at a desired level under a variety of optical conditions, including one where a plurality of lenses with different magnifications are prepared for the objective 520, the imaging lens 522 and the relay lens 523 in the inspection system shown in FIG. 2 and selectively used to change the magnifications of these lenses; one where, in one illumination method, NA is changed by the aperture stop 515; one where a polarizing beam splitter is used for the split prism 518 to provide a polarization illumination; one where the aperture stop 515 is formed in a ring shape and the mirrors 506, 507 are controlled to provide an annular illumination, one type of modified illumination; one where in one detection method, the polarization device group 519 is constructed of, for example, a half wave plate and a quarter wave plate and is controlled about an optical axis to control a diffracted light component of reflected light to provide a polarization detection; one where a spatial filter is installed at a position conjugate with the pupil 520a to shield a 0-th diffracted light and detect only higher orders of diffracted light, thus allowing for a diffracted light detection; and one where the optical condition is changed by combining the above optical conditions. The sensor output correction method of this invention therefore can produce a desirable detection result, i.e., can make the detection sensitivity uniform in the viewing field of the image sensor 521 and enhance the detection sensitivity. By giving a correction target value from the external input means 551 and sharing it among a plurality of inspection systems, this invention can provide an inspection system which eliminates contrast differences in the viewing field of the image sensor 521 and also the detection sensitivity differences among different inspection systems and in the viewing field of the inspection system.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus which detects an anomaly of a substrate, the apparatus comprising:
   an illumination system which irradiates said substrate with light, and changes a first illumination condition to a second illumination condition different from said first illumination condition;
   a detection system which detects light from said substrate, and includes a sensor, said sensor including a plurality of sensor pixels arranged in line, said detection system acquiring a first output of said sensor under said first illumination condition and a second output of said sensor under said second illumination condition;
   a processing system which acquires first data corresponding to said first output, and second data corresponding to said second output,
   wherein:
      said processing system acquires a polynomial-approximation-curve function by interpolation using said first data and said second data to calculate a correction coefficient,
      said detection system changes a sensitivity of said sensor pixels by the correction coefficient,
      said detection system acquires an image of an inspection area on said substrate by using the sensitivity of said sensor pixels changed by said function, and
   said processing system detects the anomaly of the substrate by using said image of the inspection area.

2. The inspection apparatus according to claim 1, wherein said first illumination condition is a first light intensity, and said second illumination condition is a second light intensity.

3. The inspection apparatus according to claim 1, wherein said first data is a first contrast, and said second data is a second contrast.

4. The inspection apparatus according to claim 1, wherein said processing system acquires a degree of said function by using at least one of: a substrate type, an output feature of said sensor, said first illumination condition, and said second illumination condition.

5. The inspection apparatus according to claim 1, wherein said processing system changes said function based on a surface condition of said substrate.

6. The inspection apparatus according to claim 1, wherein said output of said sensor includes said first output, said second output and another output of said sensor.

7. An inspection apparatus which detects an anomaly of a substrate, the apparatus comprising:
   an illumination system which irradiates said substrate with light;
   a detection system which detects light from said substrate and includes a sensor, said sensor including a plurality of sensor pixels arranged in a line;
   a storage system which stores a polynomial-approximation-curve function by interpolation, wherein said function is represented by using first information under a first optical condition and second information under a second optical condition different from said first optical condition,
   wherein:
      said detection system changes a sensitivity of said sensor pixels by a correction coefficient, wherein said correction coefficient is calculated using said function, said detection system acquires an image of an inspection area on said substrate by using the sensitivity of said sensor pixels changed by said function, and said processing system detects the anomaly of the substrate by using said image of the inspection area.

8. The inspection apparatus according to claim 7, wherein said first optical condition is a first illumination light intensity, and said second optical condition is a second illumination light intensity.

9. The inspection apparatus according to claim 7, wherein said first information is a first contrast, and said second information is a second contrast.

10. The inspection apparatus according to claim 7, wherein said processing system acquires a degree of said function by using at least one of: a substrate type, an output character of said sensor, said first illumination condition, and said second illumination condition.

11. The inspection apparatus according to claim 7, wherein said processing system changes said function based on a surface condition of said substrate.

12. The inspection apparatus according to claim 7, wherein said output of said sensor includes said first output, said second output and another output of said sensor.

* * * * *